United States Patent
Yamazaki

(10) Patent No.: US 9,810,793 B2
(45) Date of Patent: Nov. 7, 2017

(54) X-RAY CT APPARATUS AND DATA DETECTION SYSTEM FOR X-RAY CT APPARATUS

(71) Applicant: TOSHIBA MEDICAL SYSTEMS CORPORATION, Otawara-Shi (JP)

(72) Inventor: Masahiko Yamazaki, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 198 days.

(21) Appl. No.: 14/720,465

(22) Filed: May 22, 2015

(65) Prior Publication Data
US 2015/0253435 A1    Sep. 10, 2015

Related U.S. Application Data

(63) Continuation of application No. PCT/JP2013/081428, filed on Nov. 21, 2013.

(30) Foreign Application Priority Data

Nov. 27, 2012 (JP) .................................. 2012-258964

(51) Int. Cl.
*G01N 23/00* (2006.01)
*G01T 1/208* (2006.01)
(Continued)

(52) U.S. Cl.
CPC .............. *G01T 1/208* (2013.01); *A61B 6/035* (2013.01); *A61B 6/4233* (2013.01); *A61B 6/56* (2013.01);
(Continued)

(58) Field of Classification Search
CPC ......... A61B 6/035; A61B 6/4233; A61B 6/56; A61B 6/032; A61B 6/027; A61B 6/4085;
(Continued)

(56) References Cited

U.S. PATENT DOCUMENTS 6,844,570 B2    1/2005 Sekine et al.
8,912,499 B2    12/2014 Asagiri et al.
(Continued)

FOREIGN PATENT DOCUMENTS

CN    102193102 A    9/2011
JP    10-127619 A    5/1998
(Continued)

OTHER PUBLICATIONS

English translation of the International Preliminary Report on Patentability and Written Opinion dated Jun. 11, 2015 in PCT/JP2013/081428 filed Nov. 21, 2013.
(Continued)

*Primary Examiner* — Irakli Kiknadze
(74) *Attorney, Agent, or Firm* — Oblon, McClelland, Maier & Neustadt, L.L.P.

(57) ABSTRACT

According to one embodiment, a data detection system for an X-ray CT apparatus includes a data acquisition circuit and a connection structure. The data acquisition circuit includes at least one row of X-ray detection elements arrayed in a channel direction. The data acquisition circuit is configured to acquire data required for generating X-ray CT image data corresponding to the at least one row of the X-ray detection elements. The connection structure is configured to connect the data acquisition circuit with another data acquisition circuit directly or indirectly in a row direction.

7 Claims, 9 Drawing Sheets

(51) Int. Cl.
*A61B 6/03* (2006.01)
*A61B 6/00* (2006.01)
*G01N 23/04* (2006.01)
*G01T 1/20* (2006.01)
*G21K 1/02* (2006.01)

(52) U.S. Cl.
CPC ......... *G01N 23/046* (2013.01); *G01T 1/2018* (2013.01); *G21K 1/025* (2013.01)

(58) Field of Classification Search
CPC ......... A61B 6/583; A61B 6/5258; A61B 6/06; A61B 6/4021; A61B 6/5205; A61B 6/585; A61B 6/488; A61B 6/541; A61B 6/00; A61B 6/0457; A61B 6/4488; A61B 6/542; G01N 23/046; G01T 1/2018; G01T 1/208; G06F 3/048; G06F 3/0481; G06F 3/1423; G06F 3/1431; G06F 9/4443; G21K 1/025
USPC ....................... 378/4, 19, 98.8; 382/131, 132

See application file for complete search history.

(56) References Cited

U.S. PATENT DOCUMENTS

2003/0099323 A1* 5/2003 Nagata ................. A61B 6/032
378/4
2008/0130823 A1* 6/2008 Hagiwara ............ G06T 11/008
378/4
2012/0033784 A1 2/2012 Matsuda et al.

FOREIGN PATENT DOCUMENTS

| JP | 2003-084066 A | 3/2003 |
| JP | 2008-102088 A | 5/2008 |
| JP | 2010-243394 A | 10/2010 |
| JP | 2012-034848 A | 2/2012 |

OTHER PUBLICATIONS

International Search Report dated Dec. 17, 2013 for PCT/JP2013/081428 filed Nov. 21, 2013 with English Translation of Categories.
International Written Opinion dated Dec. 17, 2013 for PCT/JP2013/081428 filed Nov. 21, 2013.
Combined Chinese Office Action and Search Report dated Oct. 10, 2015 in Patent Application No. 201380002836.9 (with English translation of categories of cited documents).
Office Action dated Sep. 12, 2017 in Japanese Patent Application No. 2013-239808 (with unedited computer generated English translation).

* cited by examiner

X-RAY CT APPARATUS AND DATA DETECTION SYSTEM FOR X-RAY CT APPARATUS

CROSS REFERENCES TO RELATED APPLICATIONS

This is a continuation of Application PCT/JP2013/81428, filed on Nov. 21, 2013.

This application is based upon and claims the benefit of priority from Japanese Patent Application No. 2012-258964, filed on Nov. 27, 2012; the entire contents of which are incorporated herein by reference.

FIELD

Embodiments described herein relate generally to an X-ray CT (computed tomography) apparatus and a data detection system for an X-ray CT apparatus.

BACKGROUND

Conventionally, 2D (two dimensional) detector is known as an X-ray detector used in an X-ray CT apparatus. A 2D detector is an X-ray detector whose plural X-ray detection elements are two-dimensionally arranged in the channel (ch) direction and the row direction. According to a 2D X-ray detector, imaging of a wide range can be performed.

X-ray detection data detected by each X-ray detection element of an X-ray detector are output to a data acquisition system (DAS) as electrical signals. In the DAS, digitized projection data corresponding to each X-ray detection element are generated by signal processing, such as amplification, integration processing, A/D (analog to digital) conversion processing, and logarithmic transformation processing, of the X-ray detection data. In a typical X-ray CT apparatus, an X-ray detector and a DAS are integrated and installed in a rotating part of a gantry, as a data detection system.

Prior Technical Literature

[Patent literature 1] JPA 2006-113060
[Patent literature 2] JPA 2010-243394

An X-ray detector in recent years tends to have more rows of X-ray detection elements. For this reason, simplification of the structure of the data detection system including an X-ray detector and a DAS is desired. Moreover, the increase in rows of X-ray detection elements gives an important problem of heat radiation from circuits composing the DAS.

Accordingly, it is an object of the present invention to provide an X-ray CT apparatus and a data detection system for an X-ray CT apparatus which have simpler structures and can easily have many rows of X-ray detection element.

DETAILED DESCRIPTION

In general, according to one embodiment, a data detection system for an X-ray CT apparatus includes a data acquisition circuit and a connection structure. The data acquisition circuit includes at least one row of X-ray detection elements arrayed in a channel direction. The data acquisition circuit is configured to acquire data required for generating X-ray CT image data corresponding to the at least one row of the X-ray detection elements. The connection structure is configured to connect the data acquisition circuit with another data acquisition circuit directly or indirectly in a row direction.

Further, according to another embodiment, an X-ray CT apparatus includes the above-mentioned data detection system, an X-ray tube and a data processing circuit. The X-ray tube is configured to expose an X-ray to an object. The data processing circuit is configured to generate the X-ray CT image data based on projection data of the object acquired by the data detection system.

An X-ray CT apparatus and a data detection system for an X-ray CT apparatus according to embodiments of the present invention will be described with reference to the accompanying drawings.

Figure 1:
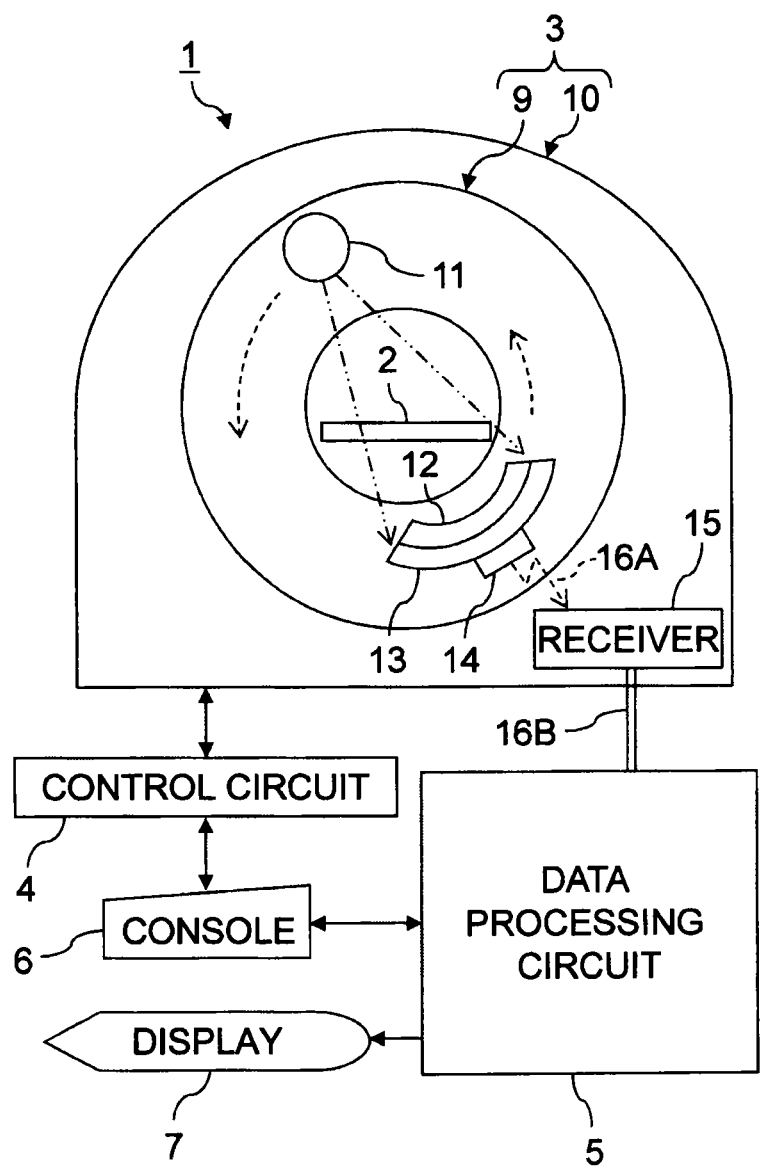
FIG. 1 is a configuration diagram of an X-ray CT apparatus and a data detection system for the X-ray CT apparatus according to the first embodiment of the present invention.

FIG. 1 is a configuration diagram of an X-ray CT apparatus and a data detection system for the X-ray CT apparatus according to the first embodiment of the present invention.

The X-ray CT apparatus 1 includes a bed 2, a gantry 3, a control circuit 4, a data processing circuit 5, a console 6, and a display 7. The console 6 can be configured by a display and an input circuit such as a mouse, a keyboard, a trackball, a touch panel and a touch pad. The bed 2 is arranged inside the cylindrical gantry 3 and can be sent into the gantry 3 in the state where an object has been set on the bed 2. The gantry 3 has a rotating part 9 and a non-rotating part 10.

An X-ray exposure part 11, an X-ray detector 12, a data acquisition circuit 13 which functions as a DAS, and a transmitter 14 are built in the rotating part 9. On the other hand, the non-rotating part 10 of the gantry 3 has a receiver 15. Thus, the transmitter 14 and the receiver 15 are configured so that the transmitter 14 can perform data communication with the receiver 15 through a data transmission line 16A. Meanwhile, the receiver 15 and the data processing circuit 5 are configured so that the receiver 15 can perform data communication with the data processing circuit 5 through a data transmission line 16B. In many cases, the data transmission line 16A between the rotating part 9 and the non-rotating part 10 is wireless.

The X-ray exposure part 11 has an X-ray tube and exposes an X-ray towards an object set on the bed 2 by a voltage application from a high voltage generator to the X-ray tube.

The X-ray detector 12 is arranged so as to face the X-ray exposure part 11, thereby the bed 2 is placed between the X-ray detector 12 and the X-ray exposure part 11. The X-ray detector 12 is a device for detecting X-rays which exposed from the X-ray tube of the X-ray exposure part 11 and have transmitted an object. In the X-ray detector 12, plural X-ray detection elements for two-dimensionally detecting X-rays which have transmitted an object are arrayed.

The direction parallel to the rotation plane of the rotating part 9 of the gantry 3 is called the channel direction or the fan angle direction. On the other hand, the direction perpendicular to the rotation plane of the rotating part 9 of the gantry 3 is called the row direction or the cone angle direction. Then, the plural X-ray detection elements are arrayed in the channel direction and the row direction. Therefore, the body axis direction of the object is the row direction of the X-ray detection elements.

Then, the rotating part 9 including the X-ray exposure part 11 and the X-ray detector 12 rotates around an object. Thereby, the X-ray exposure part 11 can expose a three-dimensional fan-shaped X-ray beam from 360 degree directions to an object. Meanwhile, the X-ray detector 12 can detect X-rays which have transmitted an object.

The X-ray detector 12 is integrated with the data acquisition circuit 13. The data acquisition circuit 13 acquires pieces of X-ray detection data output as electrical signals from the respective X-ray detection elements of the X-ray detector 12 to perform signal processing, such as amplification, integration processing, A/D conversion processing, and logarithmic transformation processing, of the acquired pieces of X-ray detection data. Thereby, digitalized projection data corresponding to each X-ray detection element are generated. The projection data generated by the data acquisition circuit 13 can be output to the data processing circuit 5 through the transmission channels, such as the transmitter 14, the receiver 15, and the data transmission lines 16A and 16B.

The data processing circuit 5 has a function to generate X-ray CT image data based on projection data of an object acquired by the data detection system consisting of the X-ray detector 12 and the data acquisition circuit 13. Specifically, the data processing circuit 5 has a function to generate X-ray CT image data from projection data by image reconstruction processing and a function to perform required image processing of the X-ray CT image data. The X-ray CT image data generated by the image processing can be displayed on the display 7.

The control circuit 4 controls the rotation of the rotating part 9 of the gantry 3 and the motion of the bed 2 according to direction information input from the console 6. Under the control, a helical scan and a scan at an arbitrary bed position can be performed.

The control circuit 4 and the data processing circuit 5 can be configured by a single circuit or plural circuits. The control circuit 4 and the data processing circuit 5 may be at least one CPU (central processing unit), at least one GPU (graphics processing unit), at least one ASIC (application specific integrated circuit), and/or at least one PLD (programmable logic device), such as an SPLD (simple PLD), a CPLD (complex PLD) and a FPGA (field programmable gate array).

Next, a detailed structure of the X-ray detector 12 and the data acquisition circuit 13 will be described.

Figure 2:
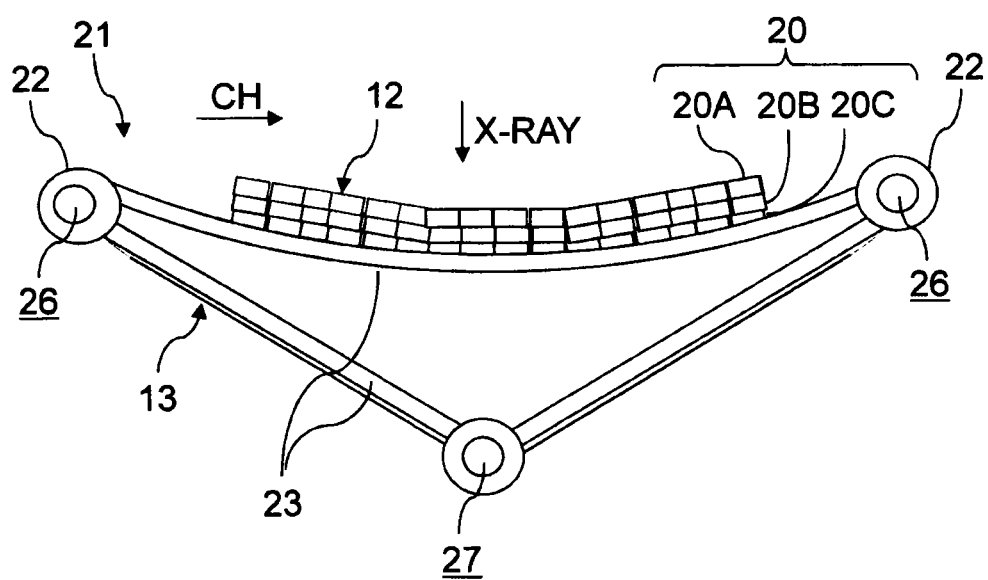
FIG. 2 is a view of the first structural example of the data detection system, consisting of the X-ray detector and the data acquisition circuit shown in FIG. 1, as viewed from the row direction.
Figure 3:
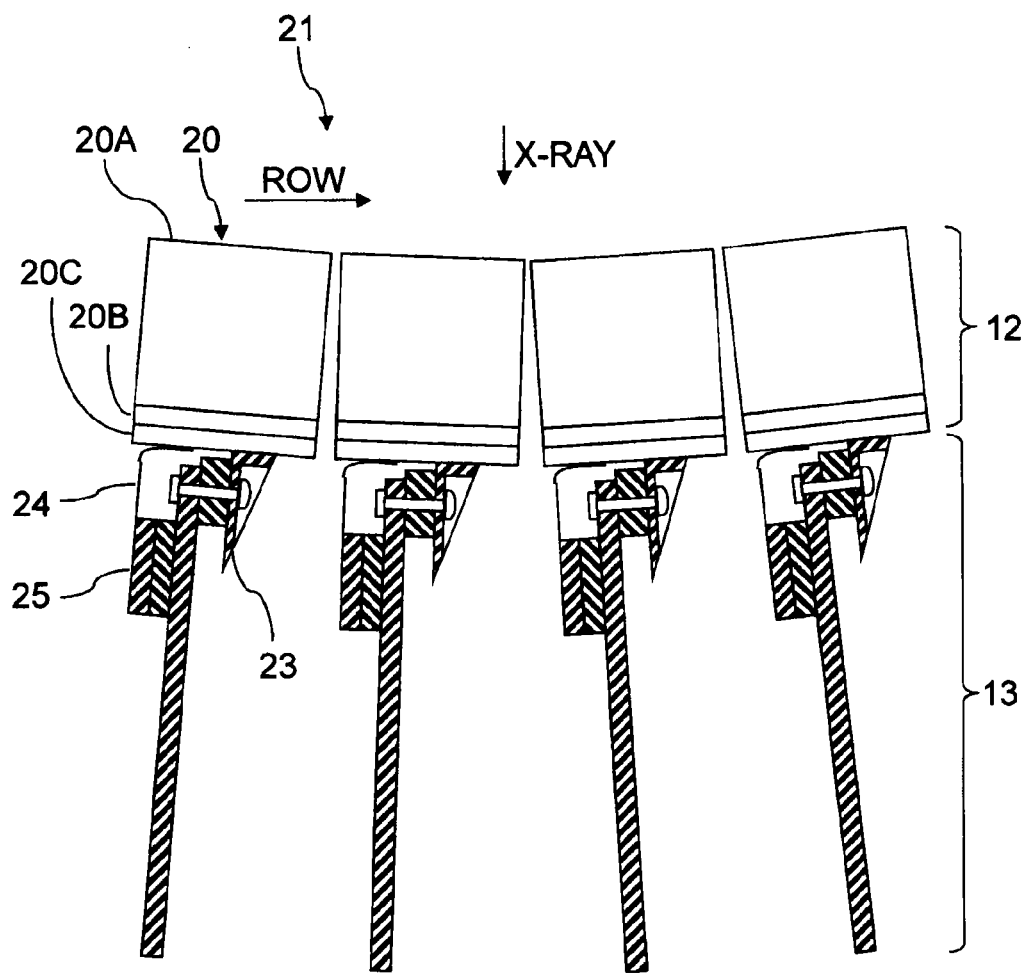
FIG. 3 is a sectional view of the data detection systems shown in FIG. 2, as viewed from the channel direction.

FIG. 2 is a view of the first structural example of the data detection system, consisting of the X-ray detector 12 and the data acquisition circuit 13 shown in FIG. 1, as viewed from the row direction. FIG. 3 is a sectional view of the data detection systems shown in FIG. 2, as viewed from the channel direction.

As shown in FIG. 2 and FIG. 3, plural X-ray detection elements 20 and plural data acquisition circuits 13 can compose plural data detection systems 21 segmented in the row direction. In other words, a single row or plural rows of the X-ray detection elements 20 and the data acquisition circuits 13 can compose the data detection system 21 as a module. Then, connected plural data detection systems 21 with each other in the row direction can compose the whole X-ray detector 12 as a 2D array detector and the whole data acquisition circuit 13 for the 2D array detector.

For this reason, each of the data detection systems 21 is configured by at least one data acquisition circuit 13 having the plural X-ray detection elements 20, and a connection structure 22 for directly or indirectly connecting the data acquisition circuit 13 with another data acquisition circuit 13 in the row direction. More specifically, the data acquisition circuit 13 composed by a platy circuit board (a backplane) has a single or plural X-ray detection elements 20 in the row direction. On the other hand, in the channel direction, the data acquisition circuit 13 has plural X-ray detection elements 20 corresponding to all the channels. That is, each modularized data acquisition circuit 13 has plural X-ray detection elements 20 in the channel direction so that data required for generating X-ray CT image data corresponding to at least one row of the X-ray detection elements can be acquired.

Therefore, the data detection system 21 can be composed by the single data acquisition circuit 13 theoretically. However, the two dimensional data detection system 21 for the X-ray CT apparatus 1 is actually composed by plural data acquisition circuits 13 connected with each other in the row direction with at least one connection structures 22. As a result, the X-ray detector 12, whose X-ray detection elements 20 are two-dimensionally arrayed in the channel direction and the row direction, is composed as a 2D array detector.

For example, the connected M data acquisition circuits 13, each having N rows of the X-ray detection elements 20, with each other in the row direction using the connection structures 22 can compose N×M rows of the data detection system 21 including the X-ray detectors 12 and the data acquisition circuits 13. Therefore, the modularized X-ray detection elements 20 and the data acquisition circuit 13 can be used for increasing and decreasing of the row number.

The shape of the circuit board mounting the data acquisition circuit 13 can be an arbitrary shape. However, the platy triangle data acquisition circuit 13 as illustrated can be attached and detached to the rotating part 9 of the conventional gantry 3. That is, when the shape of the data acquisition circuit 13 is platy triangle, the compatibility with the conventional DAS can be obtained. Moreover, the rigidity of the data acquisition circuit 13 can also be improved by forming the data acquisition circuit 13 into platy triangle.

Furthermore, a frame 23 can be installed as a reinforcement structure at each edge of the circuit board of the data acquisition circuit 13 in order to improve the rigidity of the circuit board. The data acquisition circuit 13 and the X-ray detection elements 20 are modularized for each row or each predetermined number of rows. Therefore, the thickness direction of the platy circuit board composing the data acquisition circuit 13 is different from the rotation direction of the data acquisition circuit 13. In other words, the circuit board of the data acquisition circuit 13 is approximately parallel to the rotation plane of the rotating part 9. For this reason, the strength of the circuit board of the data acquisition circuit 13 required for a rotation can be secured by reinforcing the circuit board with the frames 23.

Moreover, since the circuit board of the data acquisition circuit 13 is not orthogonal to the rotation plane, the circuit board of the data acquisition circuit 13 can be air-cooled during rotations of the rotating part 9. For this reason, the heat radiation can be attained favorably even when the number of the rows of the X-ray detection elements 20 and the number of the circuit boards for the data acquisition circuits 13 increase.

Each of the X-ray detection elements 20 mounted on the data acquisition circuit 13 is composed by overlaying a collimator 20A, a scintillator 20B, and a photodiode 20C from the incident side of X-rays. Then, an X-ray which entered the X-ray detection element 20 is formed into a parallel X-ray in the collimator 20A, and subsequently, converted into a light, whose wavelength is different, in the scintillator 20B. Furthermore, the light generated in the scintillator 20B is converted into an electrical signal in the photodiode 20C, and is output as an X-ray detection signal. Note that, in FIG. 2, the sizes of the collimator 20A, the scintillator 20B, and the photodiode 20C are illustrated approximately.

Each X-ray detection element 20 having the structure mentioned above is fixed to the end part of the data acquisition circuit 13 through the frame 23 for reinforcing the circuit board mounting the data acquisition circuit 13. As a specific example, the photodiode 20C of each X-ray detection element 20 is fixed to the end part, in the rotation axis center side, of the data acquisition circuit 13 through the frame 23 as illustrated. Therefore, the frame 23 in the rotation axis center side of the data acquisition circuit 13 also assumes the role as a connection tool between the X-ray detection element 20 and the data acquisition circuit 13.

Then, the photodiode 20C of each X-ray detection element 20 is connected with the circuit board, mounting the data acquisition circuit 13, by signal lines, which are formed as a flexible printed circuit (FPC) 24, and a connector 25. Thereby, an X-ray detection signal detected by each X-ray detection element 20 can be output to the data acquisition circuit 13.

The output side of each data acquisition circuit 13 can be connected with the transmitter 14 by an arbitrary method. For example, each data acquisition circuit 13 can be connected with the transmitter 14 using signal wires. Alternatively, the transmitter 14 may be mounted on the circuit board which composes the data acquisition circuit 13.

The connection structure 22 for connecting the data acquisition circuits 13 with each other can be configured by ring-shaped stopping tools each having a through hole 26 for passing a connection arm, for example. In the illustrated example, the ring-shaped stopping tools each having the through hole 26 for passing the connection arm are installed as the connection structure 22 at the both ends of the circuit board which composes each data acquisition circuit 13. The connection structure 22 for connecting the data acquisition circuits 13 with each other can also be used in order to attach the data acquisition circuits 13 to the rotating part 9 of the gantry 3.

In the illustrated example, the three through holes 26 and 27 are formed at the three corners of the circuit board which composes the data acquisition circuit 13. Then, the two through holes 26 in the X-ray incident side are used for connecting the data acquisition circuits 13 with each other and for attaching the data acquisition circuits 13 to the gantry 3. Meanwhile, the through hole 27 in the side far from the incident side of X-rays is used for attaching each data acquisition circuit 13 to the gantry 3. Therefore, each data acquisition circuit 13 is attached to the gantry 3 with the three through holes 26 and 27.

Figure 4:
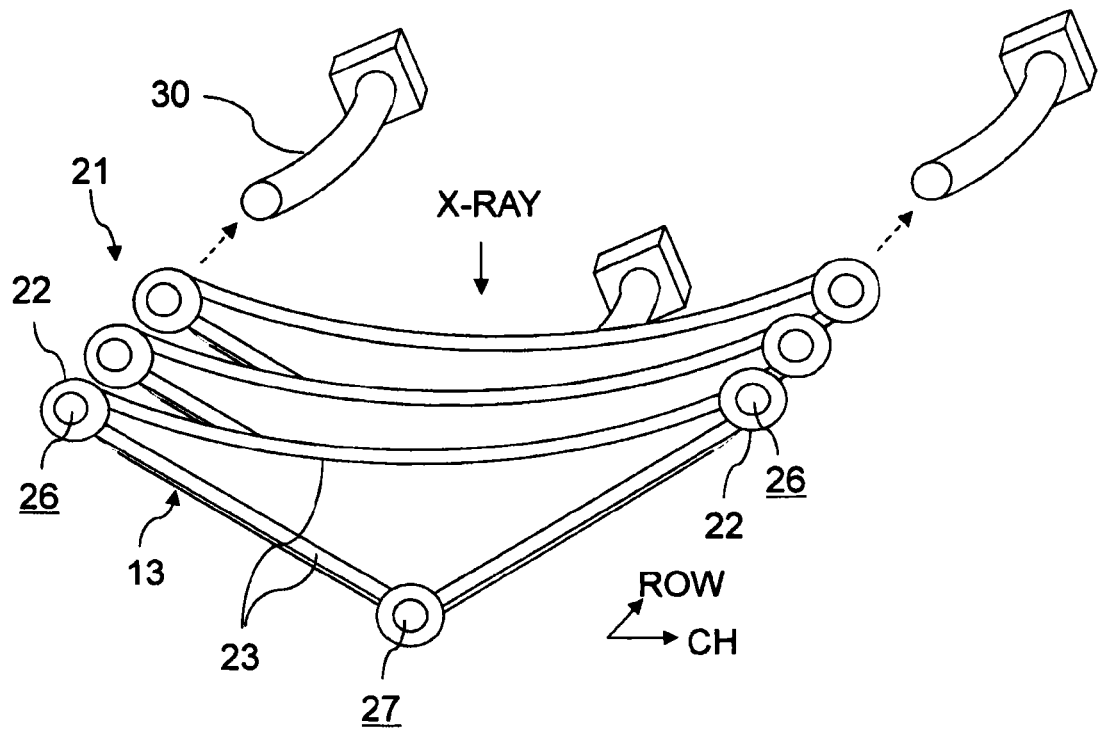
FIG. 4 is an oblique view showing a connection method of the data acquisition circuits shown in FIG. 2.
Figure 5:
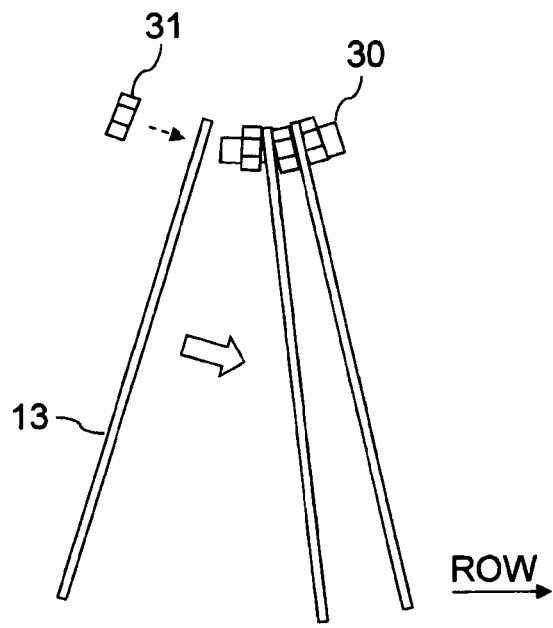
FIG. 5 is a view seen from the channel direction for explaining the connection method of the data acquisition circuits shown in FIG. 2.

FIG. 4 is an oblique view showing a connection method of the data acquisition circuits 13 shown in FIG. 2 and FIG. 5 is a view seen from the channel direction for explaining the connection method of the data acquisition circuits 13 shown in FIG. 2. Note that, illustrations of the X-ray detection elements 20 are omitted in FIG. 4 and FIG. 5.

As shown in FIG. 4 and FIG. 5, arms 30 for attaching the modularized data acquisition circuits 13 to the gantry 3 can be installed in the gantry 3 so as to adapt the positions of the through holes 26 and 27 of each data acquisition circuit 13. In the illustrated example, the arc-like curved arms 30 are installed in the gantry 3.

Thus, the plural data acquisition circuits 13 can be sequentially attached to the gantry 3 by inserting the arms 30 into the through holes 26 and 27 of each data acquisition circuit 13. Alternatively, an arbitrary attachment tool, such as an inverted L-shaped hook, may be inserted into the through hole 27 of each data acquisition circuit 13, in the side away from the incident side of X-rays, for fixing each data acquisition circuit 13 to the gantry 3, instead of the curved arm 30.

When the plural data acquisition circuits 13 are attached to the arms 30 as described above, the data acquisition circuits 13 can be connected with each other. Therefore, each arm 30 also functions as a part of the connection structure 22. Between adjacent data acquisition circuits 13, a fixing nut 31 used as a part of the connection structure 22 can be installed as a spacer. Thus, the distances between the data acquisition circuits 13 in the row direction can be adjusted appropriately by installing a spacer, such as the nut 31, which has an arbitrary structure, between adjacent data acquisition circuits 13. Moreover, the data acquisition circuits 13 and the X-ray detection elements 20 can be positioned on appropriate positions in the row direction.

Figure 6:
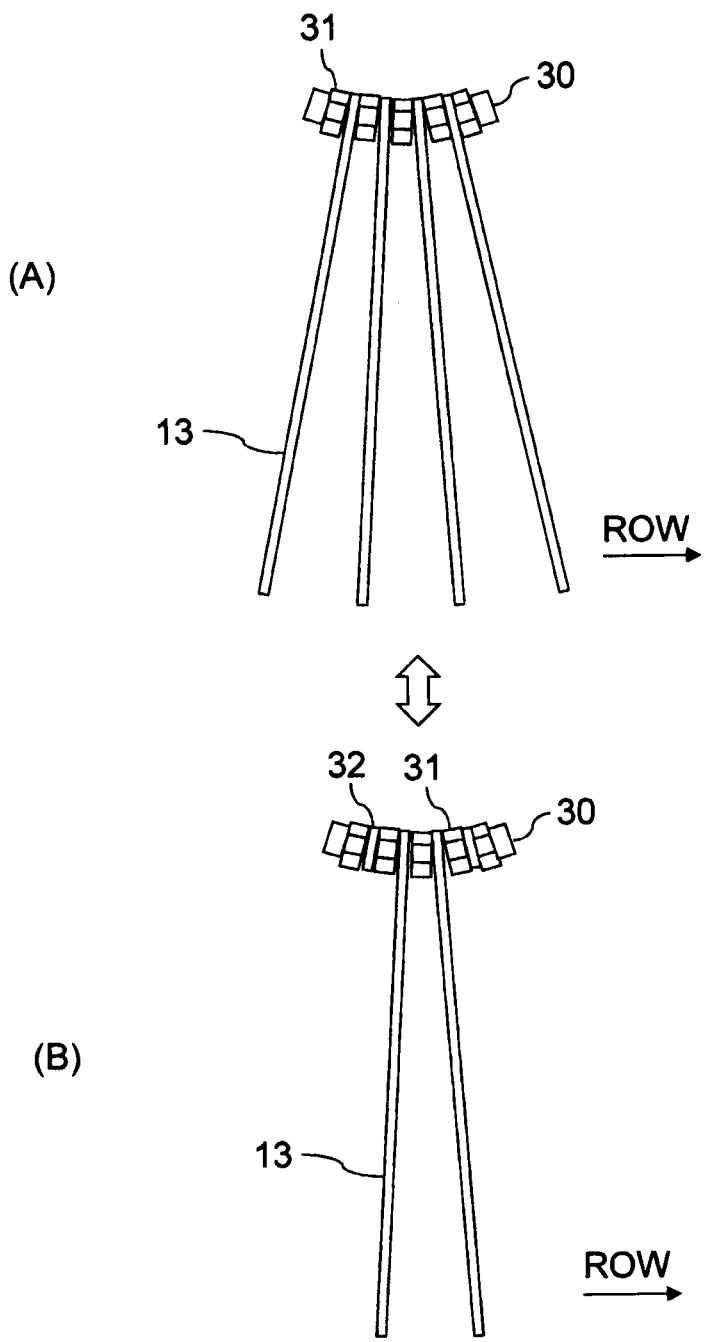
FIG. 6 is a view showing an example of adjusting the number of the data acquisition circuits shown in FIG. 2 by inserting spacers between the data acquisition circuits.

FIG. 6 is a view showing an example of adjusting the number of the data acquisition circuits 13 shown in FIG. 2 by inserting spacers between the data acquisition circuits 13.

As shown in FIG. 6 (A), the four data acquisition circuits 13 can be attached to the arms 30 and the nuts 31 which functions as fixing tools and spacers can be interposed at the both sides of each data acquisition circuit 13. On the other hand, as shown in FIG. 6 (B), the two data acquisition circuits 13 and two ring-shaped spacers 32 each having a thickness equivalent to that of the circuit board of the data acquisition circuit 13 can be attached to the arms 30, and the nuts 31 can be interposed at the both sides of the respective data acquisition circuits 13 and the two spacers 32. In this case, the X-ray detectors 12 having different numbers of rows can be composed using the nuts 31 having a same size and the arms 30. That is, the X-ray detector 12 having a desired number of rows can be composed easily using the common modules.

As a more specific example, in the case that the number of the rows of the X-ray detection elements 20 installed in one modularized data acquisition circuit 13 is 16, the X-ray detector 12 having 64 rows can be composed by attaching the four modules to the arms 30. Meanwhile, the X-ray detector 12 having 32 rows can be composed by attaching the two modules to the arms 30.

Figure 7:
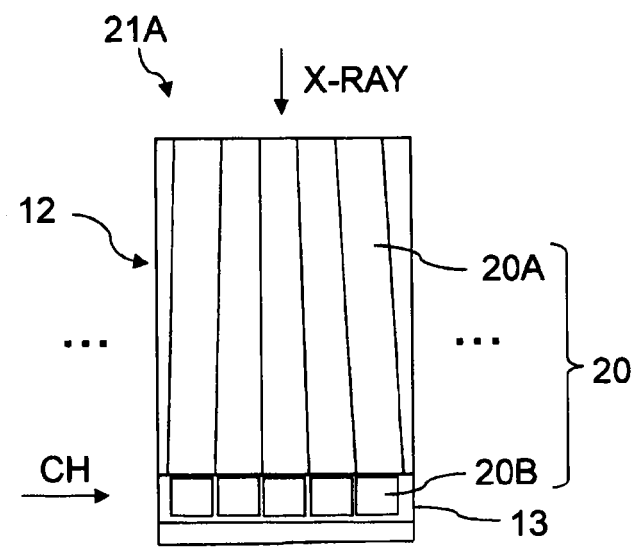
FIG. 7 is a view of the second structural example of the data detection system, consisting of the X-ray detector and the data acquisition circuit shown in FIG. 1, as viewed from the row direction.
Figure 8:
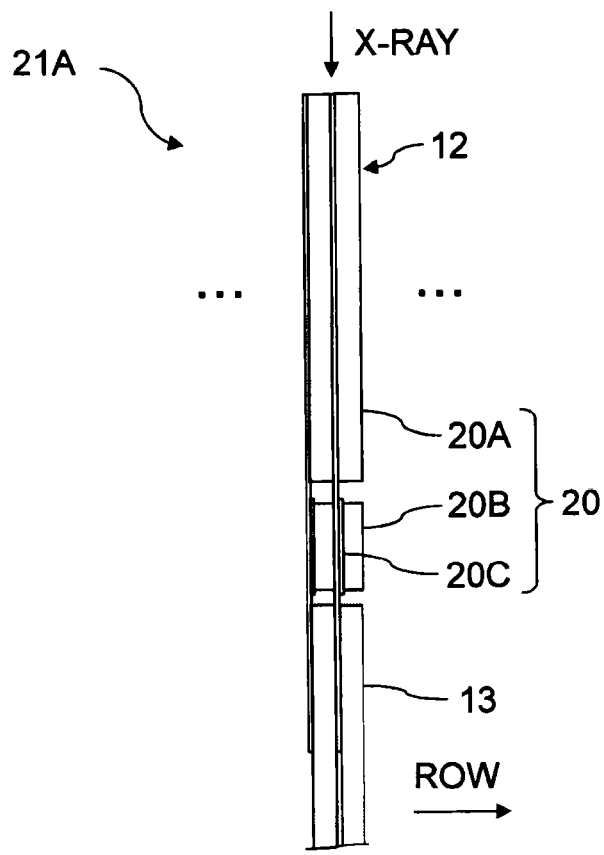
FIG. 8 is a view of the X-ray detection elements shown in FIG. 7, seen from the channel direction.
Figure 9:
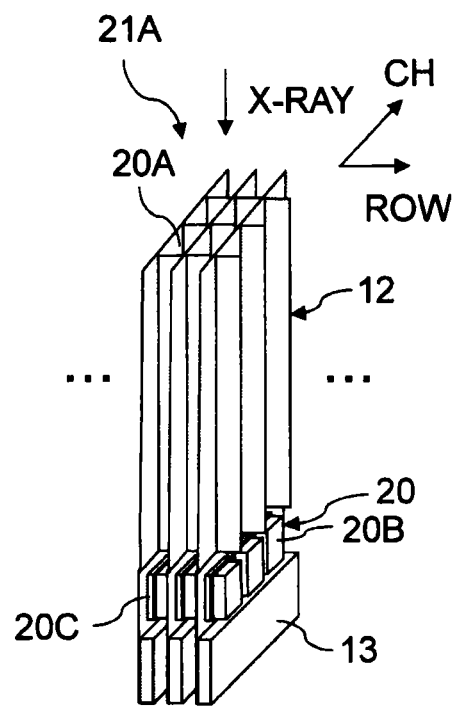
FIG. 9 is an oblique view of the data detection system shown in FIG. 7.

FIG. 7 is a view of the second structural example of the data detection system, consisting of the X-ray detector 12 and the data acquisition circuit 13 shown in FIG. 1, as viewed from the row direction. FIG. 8 is a view of the X-ray detection elements 20 shown in FIG. 7, seen from the channel direction. FIG. 9 is an oblique view of the data detection system shown in FIG. 7.

As shown in FIG. 7 to FIG. 9, a data detection system 21A can also be composed by one modularized data acquisition circuit 13, with which a row of the X-ray detection elements 20 are attached, and the scintillators 20B and the photodiodes 20C arranged in parallel to the incident direction of X-rays. That is, the platy photodiode 20C, which is mounted in each X-ray detection element 20, can be formed on the circuit board of the data acquisition circuit 13 so that the interface becomes perpendicular to the row direction. Then, the platy scintillator 20B can be bonded on the surface in the opposite side of the platy photodiode 20C which is bonded on the circuit board. Further, the collimator 20A is mounted in the X-ray incident side of the scintillator 20B.

In this case, a circuit board, such as the FPC 24 shown in FIG. 3, for connecting the photodiode 20C with the data acquisition circuit 13 is not required. That is, the signals from the photodiode 20C can be read by signal reading patterns printed on the circuit board of the data acquisition circuit 13.

Furthermore, plural X-ray detection elements 20 in each of which plural photodiodes 20C are arranged in the incident direction of X-rays can be provided with each modularized data acquisition circuit 13. That is, on the circuit board which composes the data acquisition circuit 13, the plural photodiodes 20C can be formed as a sensor part in the incident direction of X-rays. In this case, it becomes possible to acquire an X-ray detection signal for each energy level of X-ray.

Figure 10:
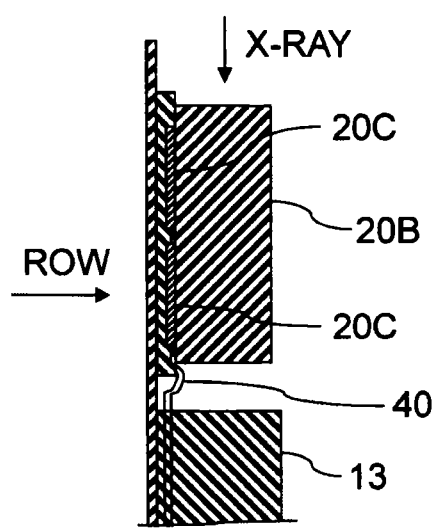
FIG. 10 is an expanded sectional view of an example of arranging two separated photodiodes in the X-ray incident direction, seen from the channel direction, in the data detection systems shown in FIG. 7.
Figure 11:
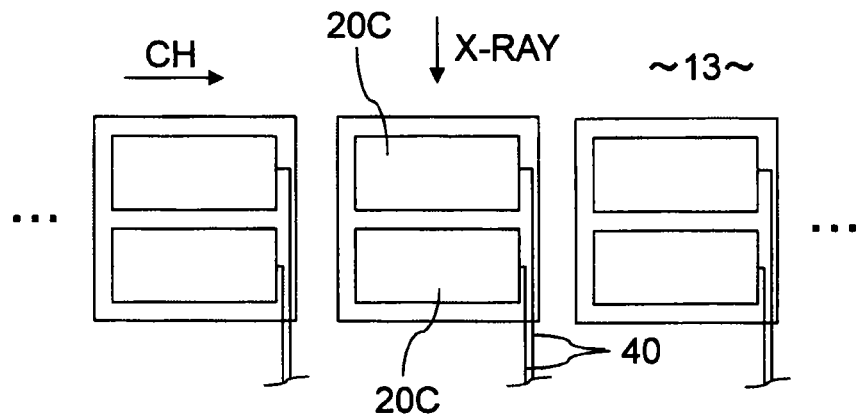
FIG. 11 is a view of the photodiodes shown in FIG. 10 as viewed from the row direction.

FIG. 10 is an expanded sectional view of an example of arranging two separated photodiodes 20C in the X-ray incident direction, seen from the channel direction, in the data detection systems 21A shown in FIG. 7. FIG. 11 is a view of the photodiodes 20C shown in FIG. 10 as viewed from the row direction.

As shown in FIG. 10 and FIG. 11, the two photodiodes 20C can be mounted in the incident direction of X-rays. Each photodiode 20C is connected with the signal processing circuit of the data acquisition circuit 13 by a signal readout pattern which forms an independent signal line 40.

In this case, the component, whose energy is relatively small, among an X-ray which has passed the collimator 20A is detected by the photodiode 20C near the incident side of X-rays because of a small transmittance of the scintillator 20B. On the other hand, the component, whose energy is relatively large, among the X-ray which has passed the collimator 20A is detected by the photodiode 20C in the side far from the incident side of X-rays because of a large transmittance of the scintillator 20B. Therefore, it becomes possible to acquire an X-ray detection signal for each energy level of X-ray. That is, the X-ray detector 12 which can acquire X-ray detection signals corresponding to dual energies can be composed.

Figure 12:
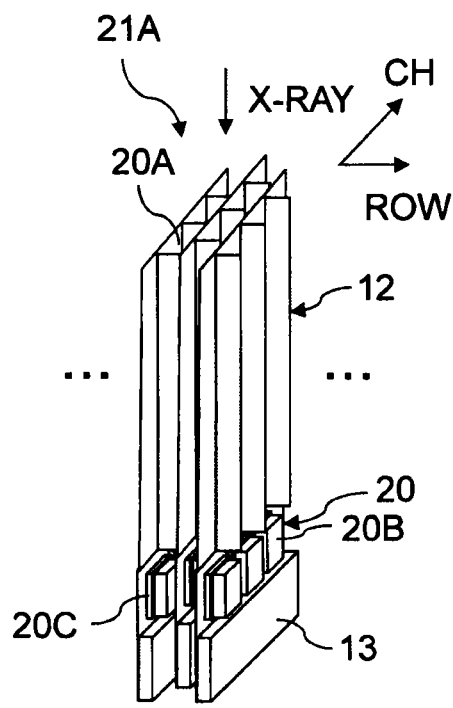
FIG. 12 is an oblique view showing a modification of the data detection systems shown in FIG. 9.

FIG. 12 is an oblique view showing a modification of the data detection systems 21A shown in FIG. 9.

As shown in FIG. 12, the positions of the X-ray detection elements 20 can be shifted in the channel direction between the data acquisition circuits 13 adjacent in the row direction. That is, the data detection systems 21A can be connected with each other with shifting the positions of the plural X-ray detection elements 20 in the channel direction for each module. Note that, the positions of the X-ray detection elements 20 between all the adjacent data acquisition circuits 13 may not be shifted, and alternatively, only the positions of the X-ray detection elements 20 attached to at least one specific data acquisition circuit 13 may be shifted.

In this case, the connection structure 22 has a structure for connecting a certain data acquisition circuit 13 with another adjacent data acquisition circuit 13 so that the X-ray detection elements 20 provided with the data acquisition circuit 13 shift from the X-ray detection elements 20 provided with the other adjacent data acquisition circuit 13 in the channel direction.

When the positions of the X-ray detection elements 20 belonging to a certain row are shifted in the channel direction as shown in FIG. 12, the sampling positions in a helical scan change for every row. For this reason, an apparent sampling pitch can be smaller and a spatial resolution can be improved.

Note that, the arrangement of the X-ray detection elements 20 as mentioned above can also be applied to the first structure example shown in FIG. 2. That is, the positions of the X-ray detection elements 20 can be shifted in the channel direction between the adjacent data detection systems 21.

Furthermore, a structure for adjusting the shift amount in the channel direction between a certain data acquisition circuit 13 and another adjacent data acquisition circuit 13 can also be installed in the data detection system 21 or 21A.

Figure 13:
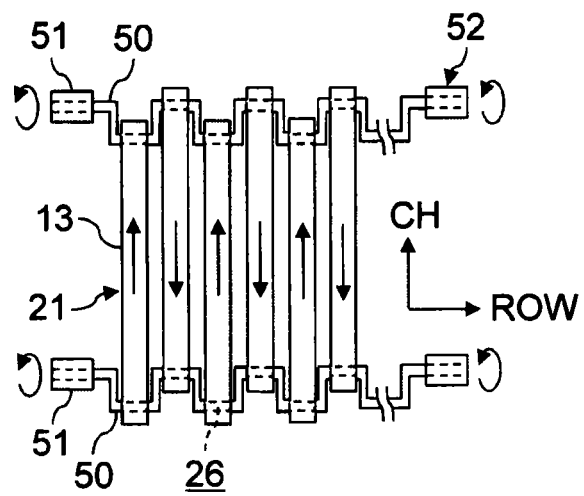
FIG. 13 is a view showing the first concrete example of adjustment structure for adjusting a shift amount between the data acquisition circuits.

FIG. 13 is a view showing the first concrete example of adjustment structure for adjusting a shift amount between the data acquisition circuits 13.

As shown in FIG. 13, an adjustment structure 52 for adjusting the shift amount between the data acquisition circuits 13 can be composed by connecting end parts of two bar-shaped structures 50, whose center axes are not coaxial, with rotation structures 51 each having a sliding bearing or the like, for example. More specifically, the distance in the channel direction between the center axes, each formed in the row direction, of each bar-shaped structure 50 arranged so that the length direction becomes the row direction can be the maximum shift amount between the adjacent data acquisition circuits 13. Thus, the shift amount between the adjacent data acquisition circuits 13 can be adjusted by rotating the bar-shaped structures 50.

Figure 14:
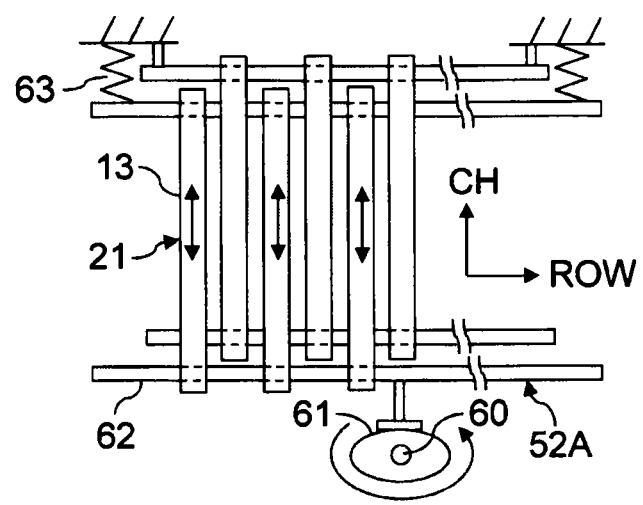
FIG. 14 is a view showing the second concrete example of adjustment structure for adjusting a shift amount between the data acquisition circuits.

In the illustrated example, each bar-shaped structure 50 has two concentric and alternate center axes corresponding to the intervals between the adjacent data acquisition circuits 13. Then, the plural data detection systems 21 can be connected with each other by inserting the two bar-shaped structures 50, having similar shapes, into the two through holes 26 at the both ends of each data detection system 21 having the structure as shown in FIG. 2. Thereby, the data detection systems 21 can be arranged alternately with a desired shift amount. As a matter of course, groups each consisting of the plural data detection systems 21 may be shifted alternately instead of shifting the data detection systems 21 alternately FIG. 14 is a view showing the second concrete example of adjustment structure for adjusting a shift amount between the data acquisition circuits 13.

An adjustment structure 52A for adjusting the shift amount between the data acquisition circuits 13 can also be configured by a link structure which reciprocates desired data acquisition circuits 13 in one direction. In the illustrated example, the link structure is composed of a rotation axis 60 and a cam 61. Then, when one of two bar-shaped structures 62, which are arranged so that their center axes shift from each other, is contacted with the cam 61, only the one bar-shaped structure 62 can be reciprocated in one direction.

For this reason, two sets, each consisting of the two bar-shaped structures 62 whose center axes shift from each other, can be arranged as illustrated. Thus, contacting one of the bar-shaped structures 62 of the first set with the cam 61 and contacting one of the bar-shaped structures 62 of the second set with an elastic body 63, such as a spring, allow parallel displacement of the two bar-shaped structures 62, away from each other by a constant distance, in one direction. On the other hand, positions of the other two bar-shaped structures 62 away from each other by a constant distance can be fixed.

Therefore, when a part of the data detection systems 21 are connected with each other by the two bar-shaped structures 62 which can be moved in parallel and the other data detection systems 21 are connected with each other by the two fixed bar-shaped structures 62, the shift amount in the channel direction between the plural data detection systems 21 connected by the two bar-shaped structures 62 which can be moved in parallel and the plural data detection systems 21 connected by the two fixed bar-shaped structures 62 can be adjusted.

The structure for adjusting the shift amount in the channel direction between the data acquisition circuits 13 may be composed using an arbitrary structure, such as a ball screw, as well as the above-mentioned examples.

The X-ray CT apparatus 1 and the data detection systems 21 and 21A as mentioned above are apparatuses, which can be independently used for an imaging scan, modularized by separating the X-ray detector 12 and the data acquisition circuit 13 in the row direction.

The conventional X-ray detector is modularized for every channel, and required for connecting plural modules corresponding to the all channels in order to perform imaging. Moreover, the number of the rows of the X-ray detection elements cannot be changed.

On the contrary, according to the X-ray CT apparatus 1 and the data detection systems 21 and 21A, a two dimensional X-ray detector having desired rows can be composed easily by connecting an arbitrary number of modules, which can be used for data acquisition independently, in the row direction. Therefore, a two dimensional X-ray detector having a desired number of rows can be composed using the same modules. Moreover, the number of rows of an already composed X-ray detector can also be changed flexibly. For this reason, it is unnecessary to make an X-ray detector and a DAS which have special structures for increasing rows of the X-ray detector. Therefore, the cost reduction can be achieved by the standardization of parts.

Moreover, the circuit board of the data acquisition circuit 13 composing one module can be arranged so as to be non-orthogonal to the rotation plane of the data acquisition circuit 13. That is, the data acquisition circuit 13 can be rotated so as not to block the air. For this reason, air cooling of the data acquisition circuit 13 can be performed using the air flow by the rotation of the gantry 3. As a result, the cooling efficiency of the data acquisition circuit 13 can be improved and the heat radiation of the data acquisition circuit 13 can be performed easily.

Moreover, shifting positions of X-ray detection elements 20 in the channel direction between rows allows the improvement of a spatial resolution in a helical scan. Meanwhile, arranging plural photodiodes 20C in the incident direction of X-rays allows the acquisition of X-ray detection signals according to energies of the X-rays.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A data detection system for an X-ray CT apparatus comprising:
    a data acquisition circuit, including at least one row of X-ray detection elements arrayed in a channel direction, and configured to acquire data required for generating X-ray CT image data corresponding to the at least one row of the X-ray detection elements; and
    a connection structure configured to connect said data acquisition circuit with another adjacent data acquisition circuit directly or indirectly in a row direction, the X-ray detection elements installed in said data acquisition circuit shifting from X-ray detection elements installed in the another adjacent data acquisition circuit in the channel direction; and
    an adjustment structure configured to adjust a shift amount in the channel direction between said data acquisition circuit and the another adjacent data acquisition circuit.

2. The data detection system for the X-ray CT apparatus of claim 1,
    wherein said data acquisition circuit includes a platy circuit board whose thickness direction is different from a rotation direction of said data acquisition circuit.

3. The data detection system for the X-ray CT apparatus of claim 1,
    wherein said data acquisition circuit has X-ray detection elements, each having photodiodes arranged in an incident direction of an X-ray.

4. The data detection system for the X-ray CT apparatus of claim 1,
    wherein said data acquisition circuit includes a platy circuit board,
    a photodiode installed in each of the X-ray detection elements is on the platy circuit board, and
    a boundary face between the photodiode and the platy circuit board being perpendicular to the row direction.

5. The data detection system for the X-ray CT apparatus of claim 1,
    wherein said data acquisition circuit includes plural X-ray detection elements in the row direction.

6. A data detection system for the X-ray CT apparatus of claim 1, including:
    said data acquisition circuit; and
    the another adjacent data acquisition circuit connected with said data acquisition circuit in the row direction by said connection structure.

7. An X-ray CT apparatus comprising:
said data detection system of claim 1;
an X-ray tube configured to expose an X-ray to an object; and
a data processing circuit configured to generate the X-ray CT image data based on projection data of the object acquired by said data detection system.

* * * * *